United States Patent [19]

Wilson

[11] Patent Number: 4,788,429

[45] Date of Patent: Nov. 29, 1988

[54] DEVICE AND METHOD FOR MEASURING BONE MINERAL MASS

[75] Inventor: Charles R. Wilson, Wauwatosa, Wis.

[73] Assignee: The Medical College of Wisconsin, Inc., Milwaukee, Wis.

[21] Appl. No.: 854,149

[22] Filed: Apr. 21, 1986

[51] Int. Cl.$^4$ .................. G01T 1/20; G01N 23/08
[52] U.S. Cl. ...................... 250/363 S; 250/362; 378/53; 378/154
[58] Field of Search ............ 128/654, 659; 250/362, 250/363 SH, 361 R, 363 R; 378/53, 154

[56] References Cited

U.S. PATENT DOCUMENTS

| | | | |
|---|---|---|---|
| 2,605,427 | 7/1952 | Delhumeau | 378/154 |
| 3,996,471 | 12/1976 | Fletcher et al. | 250/363 R |
| 4,039,841 | 8/1977 | Lerghley | 378/154 |
| 4,247,774 | 1/1981 | Brooks | 250/367 |
| 4,511,799 | 4/1985 | Bjorkholm | 250/367 |
| 4,513,078 | 4/1985 | Sandrik et al. | 430/496 |

OTHER PUBLICATIONS

Raikar et al., "Determination of Mineral Content in Bone by Photon Transmission Using Scintillation Camera", Int. J. Nucl. Meas. & Biol. (GB), 2 (4), Oct. 1975, pp. 178–180.
Hine and Sorenson, Instrumentation in Nuclear Medicine, vol. 2, Academic Press, 1974, pp. 363, 364.
Madsen, Vertebral & Peripheral Bone Mineral Content by Photon Absorptiometry, 1977, Investigative Radiology, vol. 12, pp. 185–188.
Mazess, Third International Congress on Bone Mineral Measurement, 1976, pp. 1273–1275 and 1277–1279 (Horsman, Price, Strash).
Wilson and Madsen, Dichromatic Absorptiometry of Vertebral Bone Mineral Content, 1977, Investigative Radiology, vol. 12, pp. 180–184.
Genant and Boyd, Quantitative Bone Mineral Analysis Using Dual Energy Computed Tomography, 1977, Investigative Radiology, vol. 12, pp. 545–551.
Dunn, Wahner, Riggs, Measurement of Bone Mineral Content in Human Vertebrae and Hip by Dual Photon Absorptiometry, 8/80, Radiology, vol. 136, pp. 485–487.
Bright, McManaman and Strash, Trans-Imaging of Bone Allografts—A Rapid Method for Evaluating Osseous Incorporation, 1973, Int. Conf. on Bone Mineral Measurements, pp. 293–301.
Speller, Ensell, A System for Dual-Energy Radiography, 7/83, British Journal of Radiology, vol. 56, pp.46–465.
LeBlanc, Evans, Jhingran & Johnson, High Resolution Bone Mineral Densitometry with a Gamma Camera, 1984, Phys. Med. Biol, 29(1), pp. 25–30.
Wahner et al., Dual-Photon Gd-153 Absorptiometry of Bone, 1985, Radiology, pp. 203–206.
Levy, Hoory and Bandyopadhyay, Estimation of Bone Mineral Content Using Gamma Camera: A Real Possibility?, The Journal of Medicine, No. 88, 6/85, p. 24.

*Primary Examiner*—Carolyn E. Fields
*Attorney, Agent, or Firm*—Quarles & Brady

[57] ABSTRACT

An attachment for a scintillation camera to enable the camera to be used for measurement of bone mineral mass includes a grid holder adapted to be attached to the camera, a grid mounted on the grid holder and adapted to lie directly in front of the camera when the grid holder is attached to the camera, and an arm attached at one end to the grid holder and, at the other end, including a source holder. The source holder is entirely closed except that it defines an aperture directed toward the grid. The source holder is at least 50 cm from the grid, and the grid is focussed on the source holder.

12 Claims, 3 Drawing Sheets

DEVICE AND METHOD FOR MEASURING BONE MINERAL MASS

BACKGROUND OF THE INVENTION

This invention relates to an apparatus and method for measuring bone mineral mass using photon absorptiometry.

Osteoporosis is a major health problem in our elderly population and is a major cause of bone fracture in post-menopausal women. As many as one in four post-menopausal women in the American population have had a vertebral fracture, and incidence of femoral neck fracture also increases with age. Bone is constantly remodeled during life, being resorbed and deposited to meet the changing physical and chemical needs of the body. After maturity, and especially in post-menopausal women, bone's resorption rate exceeds its rate of formation, and bone is progressively lost from the skeleton. The rate at which bone is lost is greater in women than in men, an different bones in the body appear to lose mass at different rates, with bones primarily composed of trabecular bone (i.e. vertebrae and hip) losing mass more rapidly than other bones of the body. This decrease in bone mass weakens the skeleton and causes an increase in risk of fracture. The typical kinds of fractures that are found due to osteoporosis are hip fracture and vertebral collapse, caused by a minor fall or other accident involving little trauma which would be of no consequence to the normal individual.

Bone strength, or resistance to fracture, depends primarily on the bone mass. Studies have found the maximum compressive strength of vertebral trabecular samples or vertebral bodies to be closely related to the mass of bone or mass per unit volume. There is not good correlation between the bone mass in the arm and bone mass in the spine or hip. Therefore, although it is easier to measure bone mass in the arm, it is essential to measure the spine or hip directly if an estimate of strength in those locations is desired. Also, because the loss of bone mineral mass may be as low as one percent per year, the measurements must be very accurate and precise in order to be of clinical use.

Many methods have been used in the past in order to measure the bones and bone strength in live human beings. Radiographic techniques (X-rays) are well known in the art. Standard radiographic techniques have been used to measure the dimensions and contours of bones but have not been successfully used to accurately measure bone mass.

Dual energy CT measurements have been made, but they require high dosages of radiation and are at this time relatively impractical to conduct. Single energy CT measurements are inaccurate because of the presence of unknown amounts of fat in the marrow space of the bone.

In the nuclear medicine field, a single energy photon absorptiometry technique using radioactive material was developed by Cameron and Sorensen to measure the bone mass in sections of a human arm. A radioactive source such as I-125 supplied the high energy radiation. A scanner was used, and measurements of the radiation transmitted through the arm were taken point by point as the scanner scanned across the arm. The accuracy of these results was quite good, but this technique could not be used to accurately measure bone mass in the spine or hip, due to non-uniformities in the medium through which the photons pass (i.e., gas bubbles in the abdomen, etc.). It was found that dual energy techniques were required in order to eliminate the uncertainties due to the variation in patient thickness over the area of the scan.

The dual energy technique using high energy radiation and a rectilinear scanner is limited in terms of resolution. The rectilinear scanner does a point by point measurement, which takes 20 to 40 minutes to conduct. If it were practical to conduct a ten hour scan on an individual person, good resolution could be obtained; however, if a reasonable time period and reasonable radiation dosage are to be used, only a limited number of data points can be measured, resulting in limited resolution. Due to the relatively poor resolution obtained by this method, it is difficult to precisely distinguish between different regions of the bone. In addition, it is difficult to keep the patient still for this long period, and any motion of the patient during the scan can adversely affect the results. The limitations of the rectilinear scanner make it impractical to obtain an accurate lateral view of the spine, so only a frontal view is obtained. The frontal view does not permit a separate analysis of the load-bearing portion of the vertebrae, which is possible with a lateral view.

A gamma camera has an advantage over a rectilinear scanner in that it can receive data from all points of the bone at approximately the same time, receiving something akin to a radiograph taken all at once as opposed to the long, point by point reception of the rectilinear scanner. This enables the person operating the camera to receive considerable information much faster than with a rectilinear scanner. However, there are serious problems with the accuracy of the results of measurements done with the gamma camera due to scatter radiation.

A few studies have been conducted using a gamma camera to measure excised bones or thin parts of an animal's body, but they have not produced results which are useful for clinical practice in measuring the spine or hip where substantial scatter is present. In the measurement of bone minerals using a gamma camera, the amount of bone mineral present is calculated based on the amount of radiation that gets through the bone and into the detector. It is assumed that all the radiation which reaches the detector has passed straight through the bone and tissue. However, when the bone is surrounded by a thick layer of tissue, as in the chest or abdomen, there is substantial scatter radiation—radiation which is not absorbed but changes direction and energy as it passes through the body. The gamma camera is unable to completely distinguish between the scattered radiation and the primary radiation which has followed a straight path, and this scatter radiation creates substantial inaccuracies in the results.

As will be described later, the present inventor has tested the effect of the scatter radiation on mineral measurements by measuring an aluminum bar (1 cm wide by 3.1 mm thick) in different scattering conditions. The tests found that scatter radiation from photons passing through a mass similar to that presented by the human chest or abdomen caused the measurements to be in error, with the measured mineral content of the aluminum bar being approximately one-half of the actual value. Clearly, an error of 50% is not acceptable in measuring the spine and hip of clinical patients to determine whether they are losing bone mineral mass. Moreover, this error varies depending upon patient thickness.

There are no useful suggestions in the nuclear medicine art for methods to reduce the scatter. One textbook reference which mentions the possibility of transmission imaging of the human body using a scintillation camera says that the "skeletal anatomy cannot be used for reference because it cannot be seen," and it suggests that a parallel-hole collimator could reduce scatter. See *Instrumentation in Nuclear Medicine*, edited by Gerald J. Hine and James A. Sorenson, Volume 2, Academic Press, New York and London 1974, pp. 363–364. Given that advice, it is no wonder that no good skeleton images had been reported. As will be explained later, the standard parallel-hole collimator would have prevented the primary photons from reaching the camera and forming an image.

In nuclear medicine, the field for which the gamma camera was developed and in which it has been used, the gamma camera is used to detect radiation coming from radioactive materials that have been absorbed by organs in the human body. The person is placed directly beneath the camera so that the radioactive source (the organ that has absorbed the radioactive material) is very close to the camera. Since the radioactive material radiates in all directions, it is common to place a collimator between the radiation source and the camera to ensure that only rays which are coming straight from the source enter the camera in order to form an image of the organ. The purpose of the collimator in this context is not to eliminate scatter but rather to allow the camera to see only photons originating directly below the camera. The collimator is a thick lead plate with a large number of holes and relatively large septa between the holes. The typical nuclear medicine collimator is about three centimeters thick, which holes having a diameter of 2–3 millimeters, and the walls (septa) separating the holes are about 0.3 mm thick.

The collimators either have parallel holes (unfocussed) or are converging (focussed) at a point close to the gamma camera. An unfocussed (parallel-hole) collimator cannot be used for eliminating scatter in the measurement of bone minerals, because, in making bone mineral measurements, the source of the radiation is not directly below the camera but is spaced a distance away (at least as far away as the thickness of the patient), and, therefore, the photons which reach the collimator almost all enter at an angle, not parallel to the direction of the holes in the collimator. Since the parallel-hole collimator stops all photons except those travelling parallel to the holes, it would not only eliminate the scatter but would also attenuate the primary photons, thereby preventing the image from reaching the camera. A conventional converging collimator is focussed at about 30 to 40 cm, and this short focal length would also cause the collimator to attentuate the primary photons when measuring the spine or hip. In addition, the resolution of any image which could pass through a standard nuclear medicine collimator would be limited to about 1.5 line pairs per centimeter, which is not adequate resolution for distinguishing vertebrae in osteoporotic individuals. Thus, a collimator would not be useful for eliminating scatter when imaging the human spine or hip.

In short, due to the inaccuracies in measurements caused by scatter, it was not possible to take advantage of the benefits of the gamma camera for accurately measuring bone mineral mass in the spine or hip before the present invention was made. In addition, there was no practical technique for making accurate lateral measurements of the spine prior to the present invention.

SUMMARY OF THE INVENTION

The purpose of the present invention is to reduce the inaccuracies previously associated with the gamma camera in bone mineral measurements in order to take advantage of the gamma camera's abilities to gather data from many points almost simultaneously, to quickly measure bone mass with good resolution and with low radiation dosages, and, specifically, to accurately measure bone mass in areas of the body such as the spine and hip in which fractures due to osteoporosis are most likely to occur and in which accurate measurements were previously very difficult to obtain. In addition, the purpose of the present invention is to provide an apparatus which measures bone mineral with enough accuracy and resolution to permit lateral measurement of the spine for analysis of only the load-bearing portions.

The present invention uses a dual photon absorptiometric technique in which a gadolinium 153 source or other suitable source(s) and a gamma camera (scintillation camera) are used. The bone or bone segment in alive human is placed between the radiation source and the gamma camera, and there is a substantial distance between the bone and the camera so that a magnified image of the bone appears at the camera. In addition, a radiographic grid is placed between the bone sample and the camera in order to reduce scatter radiation. The radiographic grid is known in the field of X-rays or radiographs but has not previously been used in the nuclear medicine field. The radiographic grid is usually less than one centimeter thick, with spaces less than one millimeter wide and wall thickness (septa) less than 0.1 mm. Radiographic grids are usually focussed and are specified as a certain number of lines per inch, i.e. 70 lines per inch. The use of a magnified image, an air space between the individual and the camera, and a radiographic grid directly in front of the camera greatly improve the accuracy of the results by eliminating scattered photons so that the gamma camera becomes very useful in measuring bone mineral mass. From the preliminary test that have been conducted using this set-up, it is expected that measurements with an accuracy of 96–98% will be obtained with the present invention.

The data obtained from the gamma camera include two matrices of numbers, each corresponding to the transmission of primary photons at its respective energy level emitted from the radiation source at points along the bone. Each matrix is essentially a digital radiograph of the bone and can be displayed pictorially by means of a cathode ray tube or by other known means. These data can be analyzed to give the bone mineral mass at each point in the image, and this bone mineral distribution can be analyzed for selected regions of the bone. For example, a lateral view of a portion of the spine may be made and only the anterior (load-bearing) portion analyzed.

DESCRIPTION OF THE PREFERRED EMBODIMENT

Figure 1:
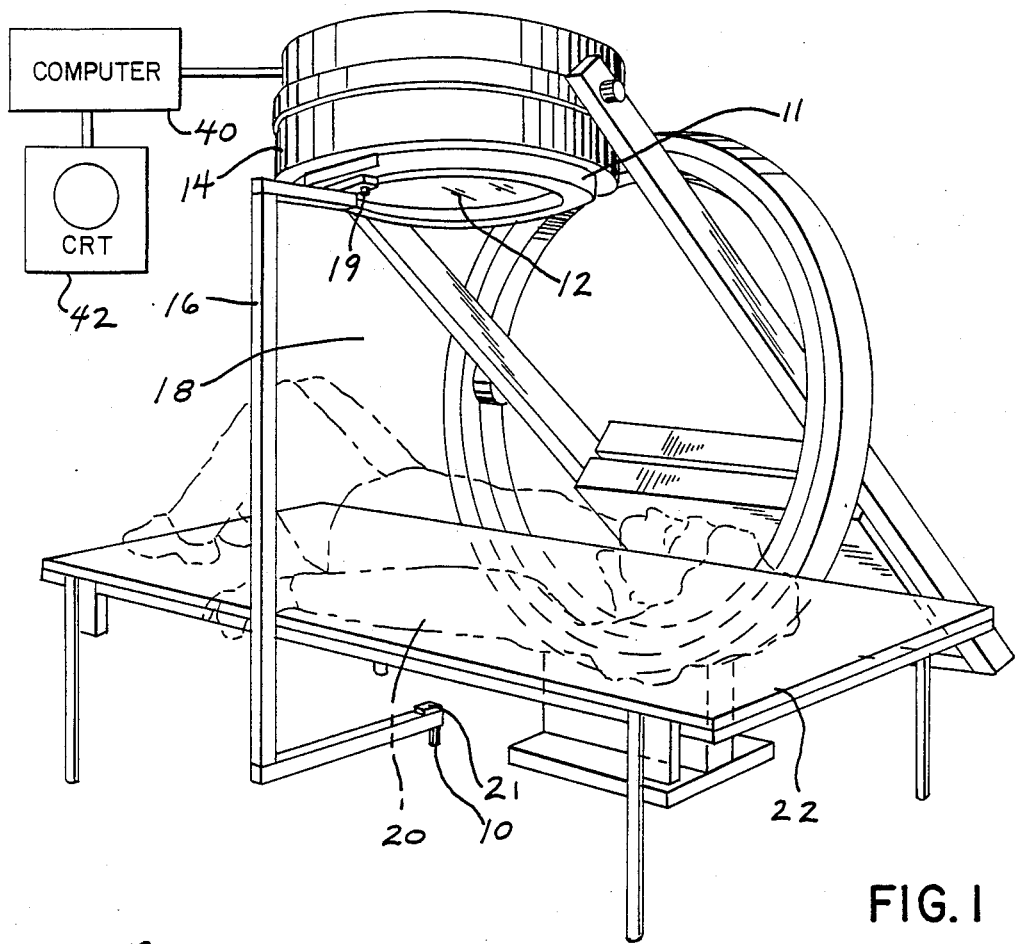
FIG. 1 is a schematic view of the gamma camera arrangement of the present invention oriented to provide a frontal view of the vertebrae.
Figure 2:
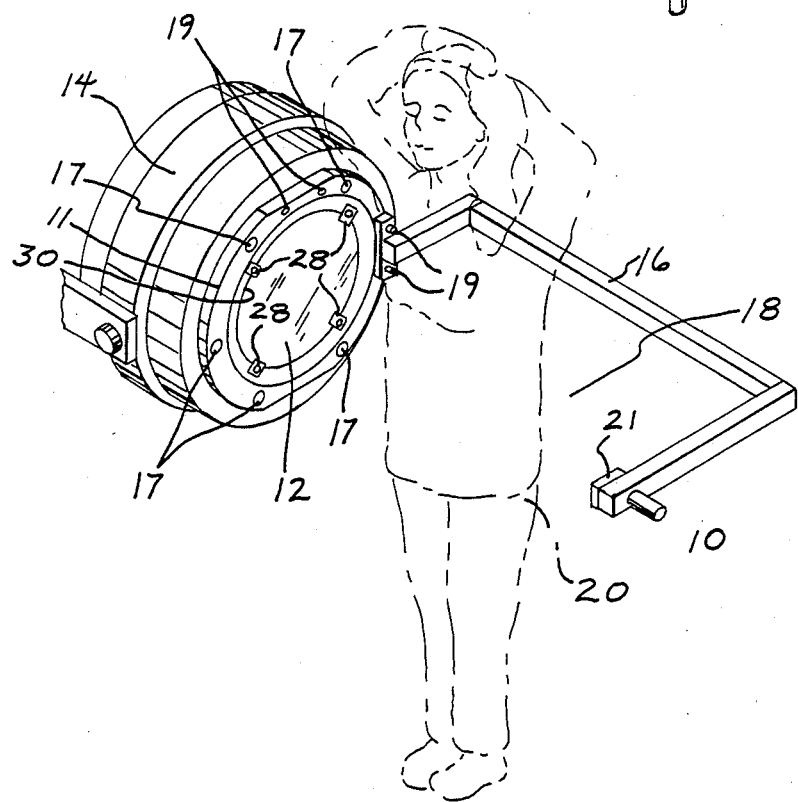
FIG. 2 is a schematic view of the arrangement of the present invention oriented to provide a lateral view of the vertebrae.

As shown in FIGS. 1 and 2, the set-up used in the present invention includes a radiation source holder 10, a grid holder 11, a radiographic grid 12, and a scintillation camera 14. The source 10, grid 12 and camera 14 are held a fixed distance apart by means of a C-shaped bracket 16, with the source 10 directed toward the center of the camera 14. The grid holder 11 is bolted at bolts 17 to the head of the camera 14. The C-shaped bracket 16 is bolted at one end by bolts 19 to the grid holder 11, and its other end carries the source holder 10.

Figure 3:
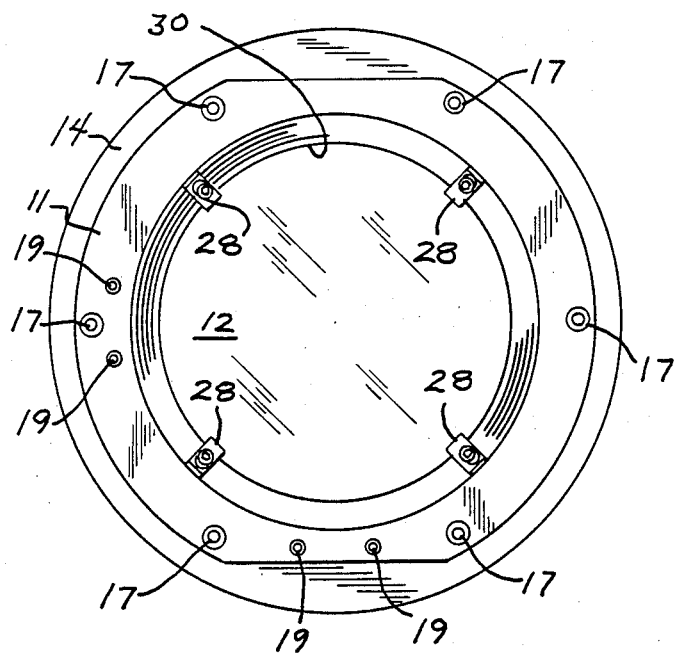
FIG. 3 is a front view of the gamma camera, including the grid holder and grid but with the bracket removed.

In FIG. 3, the bracket 16 has been removed, and it can be seen that there are two sets of bolts 19, one on the left side and one on the bottom, so that the bracket can be mounted either at the left side or bottom of the ring 11. The bracket 16 defines a space 18 in which a human subject 20 may be placed. The person 20 may recline on a couch or table 22 (as in FIG. 1) or may stand in the space 18 provided by the bracket 16 (as shown in FIG. 2). The exact position of the person 20 relative to the source holder 10 and camera 14 depends upon the area of the person 20 which is to be analyzed. In FIG. 1, the person is oriented for a frontal view of the spine, and in FIG. 2, the person 20 is oriented for a lateral view of the spine. The source 10 may be directed toward the person's pelvis, spine, or other bones to be measured, and the person 20 may face the source 10 or be oriented at an angle to the source, depending upon the analysis to be done.

Figure 5:
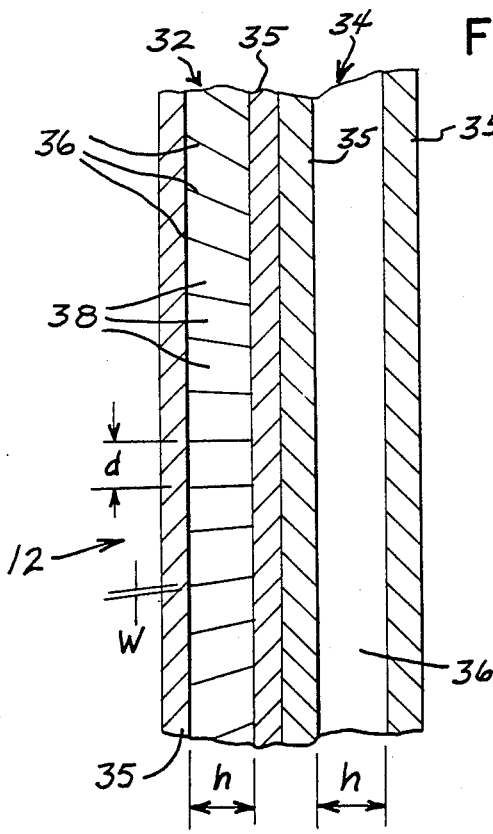
FIG. 5 is a schematic view along the section 5—5 of FIG. 4.
Figure 6:
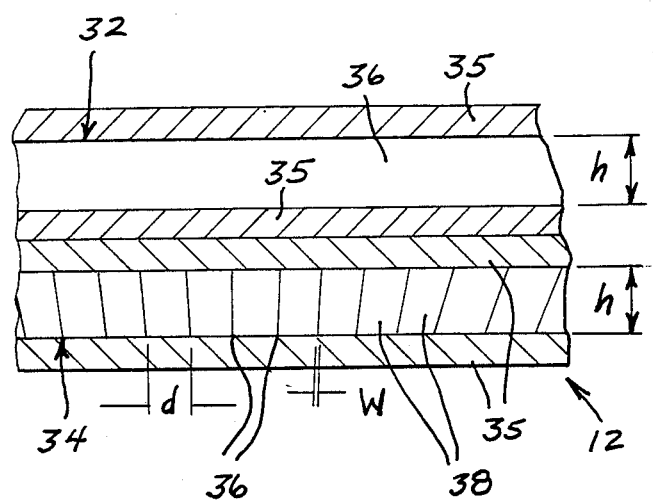
FIG. 6 is a schematic view along the section 6—6 of FIG. 4.
Figure 7:
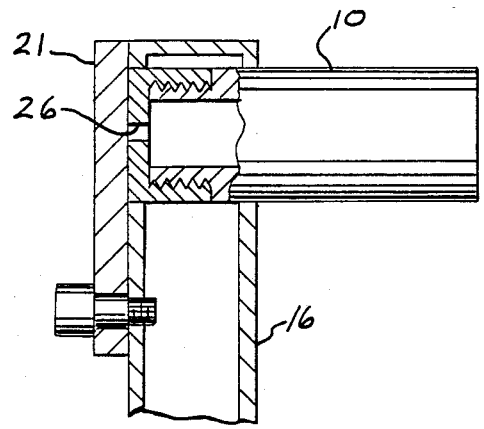
FIG. 7 is an enlarged view partly in section of the end of the bracket and the source holder.

The source holder 10 (shown in detail in FIG. 7) is simply a cylinder closed at both ends. A lead shutter 21 is placed in front of the source 10 and is pivotably connected to the bracket 16 to prevent unnecessary exposure to the radiation while the patient is being positioned. When the shutter is rotated to the open position, a beam of radiation leaves the source holder 10 through its only aperture 26 having a diameter of up to 5 mm (preferably less than 3 mm), which is directed toward the center of the grid 12 (and the center of the camera 14). The radiographic grid 12 is actually a pair of focussed radiographic grids 32, 34, as shown in FIGS. 5 and 6, which are oriented to form a cross-focussed grid. The grids 32, 34 are held onto the front of the gamma camera 14 directly in front of the camera's crystal 15, by means of clips 28 spaced around the inner edge of and bolted to the lead ring 11, which, in turn, is bolted to the gamma camera head. The grid 12 is sized to completely cover the opening 30 that is defined by the lead frame 11. The opening 30 is sized approximately the same as the size of the camera's crystal, and the frame (grid holder) 11 and grid 12 completely cover the crystal of the camera 14. The grids 32, 34 against the grid holder 11 so there is no space between the grid 12 and the grid holder 11 so that radiation cannot reach the camera 14 without passing through the grid 12. The gamma camera 14 shown in this embodiment is a General Electric 400T, but other scintillation cameras could also be used, and a bracket and grid mounting apparatus would then be made to fit on those cameras.

Figure 8:
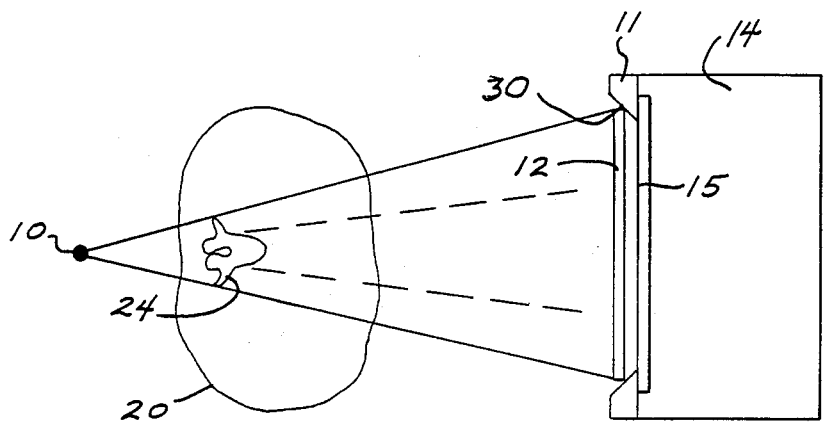
FIG. 8 is a schematic view of the present invention being used to make a frontal image of the spine.

It is preferred that the bone or portion of bone to be analyzed be located at least 30 cm from the camera's crystal 15 so that the image received by the camera will be magnified. In the set-up shown in FIGS. 1 and 8, the source holder 10 is placed approximately 1 meter from the crystal 15 of the gamma camera 14. The bone 24 is located approximately 30 cm from the source 10, 70 cm from the grid 12 and 75 cm from the camera's detector 15. As shown in FIG. 8, the photons originate at the source 10, forming a beam which becomes wider as the distance from the source 10 increases. The photons which are transmitted through the bone 24 continue through the grid 12 and to the crystal 15, with the image of the bone 24 appearing magnified on the face of the crystal 15. With this arrangement, an image magnification of about 3 is obtained. Without magnification, the resolution of this particular camera is between 1.5 and 2 line pairs per centimeter, depending upon the photon energy, but, by magnifying the image three times, the resolution becomes approximately 4.5 to 6 line pairs per centimeter, meaning that the camera can detect as many as six different data points in each centimeter length of bone. It is preferred to obtain magnification in the range of 2 to 5 times for the best results, and it is preferred that the source holder 10 be at least 50 cm from the grid 12.

The radiation source which has been used successfully with this set-up is a 50 millicurie gadolinium-153 source (about 3 mm in diameter) which is placed inside the source holder 10 by unscrewing one end of the source holder, inserting the radiation source, and then reclosing the source holder 10. It is contemplated that other radiation sources may also be used. Gadolinium-153 was chosen because it produces radiation at two different energies—one centered at 44 keV and the other at 100 keV.

Figure 4:
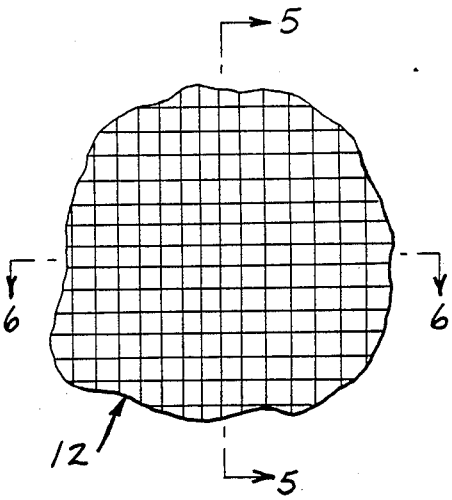
FIG. 4 is a schematic, enlarged top view of the central portion of the grid of FIG. 3.

The grid 12 is shown in greater detail in FIGS. 4–6. As was mentioned earlier, the grid 12 is actually a pair of focussed radiographic grids 32, 34, one grid rotated 90° from the other, so as to provide a cross-focussed grid. The inner grid 32 contacts or is very close to the crystal 15 of the camera 14, and the outer grid 34 contacts the outside of the inner grid 32. Each grid 32, 34 is made up of a number of flat strips (septa) 36 of lead foil with spaces 38 between the strips. The spaces 38 may be made of plastic, aluminum, or other material which serves as a structural support for the thin septa 36 without unduly interfering with the transmission of photons. In this embodiment, each grid 32, 34 has eighty of such strips 36 per inch. The height h of the lead portion of each grid 32, 34 is about 3 mm. The lead portion is sandwiched between two aluminum sheets 35. The width d of the space 38 between lead strips 36 is approximately 0.25 mm, and the grid ratio h:d is 12:1. The width w of each lead strip (septum) 36 is about 0.06 mm. The lead strips 36 are oriented at an angle so that they are focussed with a focal length of 36 to 40 inches, thereby focussing approximately on the source 10. The grids 32, 34 are oriented so that the lead strips 36 of one grid 32 are at about 90° to (or crossed with) the lead strips of the other grid 34, thereby focussing the beam in two planes (cross-focussing). Both the grids 32, 34 and the air gap between the patient 20 and the detector 14 prevent the scatter radiation arising in the patient from reaching the detector, thereby permitting very accurate measurements, and the magnified image provides very good image resolution, a combination that was not previously possible in measurements of the vertebrae and pelvis.

In this particular embodiment, the General Electric 400T camera 14 was connected to a Star computer 40, which served as an analyzer of the data, and the computer 40 was connected to a cathode ray tube 42 to provide visual images of the raw data or of the calculated results.

When photons from the gadolinium-153 source are transmitted through the patient and through the grid 12, they hit the crystal (or detector) 15 of the gamma camera 14, which produces light. The gamma camera detects that light and translates it into an electrical signal. The gamma camera 14 detects the position (x and y coordinates) of the hit and the energy of the photon. In this set-up, the computer is programmed to register a hit when the energy of the photon falls within a 25–30 percent window centered at the 44 keV (low energy) and 100 keV (high energy) emissions of gadolinium-153. (The size of the window could be smaller, i.e. 10%.) The computer 40 records the x and y coordinates of the hit and whether it is a high energy or low energy photon.

During the approximately 5-10 minutes of the measurement, the computer collects the data and constructs one matrix for each energy level indicating the number of hits in each pixel (each measured point) of the image. The raw data, then, is two matrices indicating the number of hits in each point of the image—one matrix for high energy hits and one matrix for low energy hits. The number of data points per $cm^2$ of surface of the crystal depends on the gamma camera. This particular test uses a 128×128 matrix, so it records the number of hits in each of 16,384 data points at each energy level.

The body is assumed to be composed of two materials, bone and soft tissue. The number of photons transmitted through the body at each energy is defined by the following equations:

$$I(L) = I'(L)e^{-\mu(L,S)\cdot M(S) - \mu(L,B)\cdot M(B)}$$

$$I(H) = I'(H)e^{-\mu(H,S)\cdot M(S) - \mu(H,B)\cdot M(B)}$$

with the elements of the equation being defined as follows:

I'(H)=intensity of the incident high energy photon beam
I'(L)=intensity of the incident low energy photon beam
I(H)=intensity of the transmitted high energy photon beam
I(L)=intensity of the transmitted low energy photon beam
$\mu(H,S)$=X-ray mass absorption coefficient of soft tissue at the high energy
$\mu(L,S)$=X-ray mass absorption coefficient of soft tissue at the low energy
$\mu(H,B)$=X-ray mass absorption coefficient of bone mineral at the high energy
$\mu(L,B)$=X-ray mass absorption coefficient of bone mineral at the low energy
M(S)=mass of soft tissue in the beam
M(B)=mass of bone mineral in the beam These equations can be solved for the mass of bone mineral M(B):

$$M(B) = K[(\ln I'(L) - R\cdot \ln I'(H)) - (\ln I(L) - R\cdot \ln I(H))].$$

K and R are constants given by:

$$K = \frac{\mu(L,S)}{\mu(H,S)\cdot \mu(L,B) - \mu(L,S)\cdot \mu(H,B)}$$

$$R = \frac{\mu(H,S)}{\mu(L,S)}$$

The mass absorption coefficients are determined by measuring known masses of bone and soft tissue.

The analyzer collects the matrix of data for the unknown bone, stores the data in its memory, and then uses these equations to solve for the areal mass density of bone M(B) lying in the path of the photon beam at each data point. Standard corrections are made for variations in fat and tissue composition, count rate losses due to limitations of the gamma camera, and spillover effects. These corrections are known in the art and have been described in papers dealing with rectilinear scanning techniques. By integrating M(B) over the entire bone or over a portion of the bone, the total bone mineral mass of that bone or portion of bone is determined. The raw data, i.e. the matrix of I(L) data (transmitted photons) can be translated by the cathode ray tube 42 into an image of the bone, and the matrix of calculated bone mass M(B) can then be analyzed for any area of that image. Because the image and the calculated bone mass come from the same raw data which was obtained within a short period of time and, because the resolution of the image is so good, there is no doubt as to the exact area being analyzed, and there should be no difficulty in repeating a measurement of a patient annularly, to compare bone mass in a given region from one year to the next.

With the prior art rectilinear scanners, spatial resolution is on the order of one to two line pairs per centimeter. This resolution makes it extremely difficult if not impossible to recognize anatomical features in osteoporotic individuals because of the combination of low mineral mass and poor resolution. As explained earlier, the resolution of the gamma camera with the set-up shown in FIG. 1 is approximately six line paris per centimeter of bone, and it permits a clear view of the anatomical features even in osteoporotic individuals.

This clear view of the anatomical features makes it possible to do a much more detailed analysis of the bone. For example, it may be desirable, as shown in FIG. 2, to take a lateral view of some vertebrae and do an analysis of only the anterior (load-bearing) portions of the vertebrae. Since it is this anterior portion which bears the load, an analysis of only this portion can provide much more meaningful data in the sense of predicting when the bone will fail. Also, a lateral view will eliminate the error in a frontal view which can be caused by calcification in the aorta and in soft tissues around the spine, which show up in the measurement as bone mineral. This lateral measurement is not practical with the rectilinear scanner.

Figure 10:
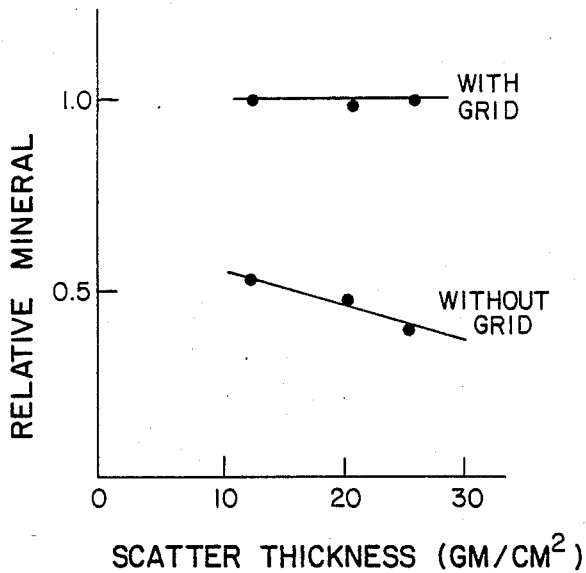
FIG. 10 is a graph of the data obtained from the test set-up in FIG. 9.
Figure 9:
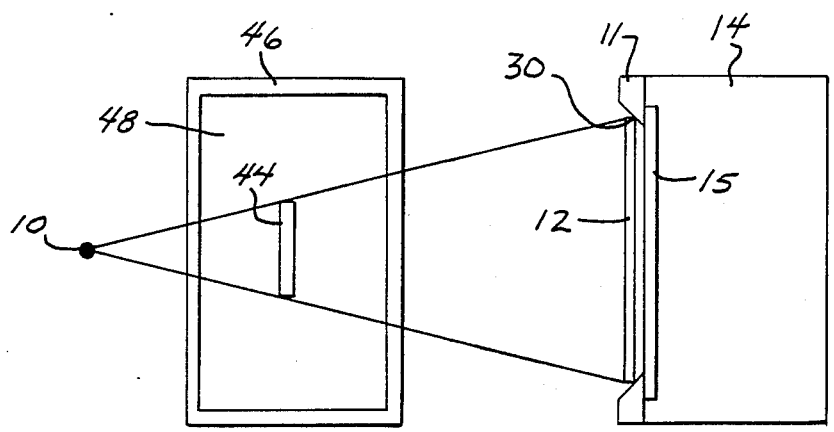
FIG. 9 is a schematic view of the present invention being used to make a test image of an aluminum bar.

To determine the extent to which the present invention eliminates scatter, as was briefly mentioned in the background section and as shown in FIGS. 9 and 10, measurements were taken of an aluminum bar 44 (1 cm wide by 3.1 mm thick) in different scattering conditions by submerging the bar in LUCITE brand of methyl methacrylate tanks 46 of different sizes holding different amounts of water 48. This provided phantoms of 12.3, 19.6, and 25.3 grams per square centimeter (i.e. 12.3 grams of LUCITE brand of methyl methacrylate and water in an imaginary column one centimeter square passing straight through the aluminum bar parallel to a line straight from the center of the source 10 to the center of the camera 14). Of course, the larger the phantom, the greater the scatter. (An average person's abdomen would provide about 25 grams per square centimeter and would be comparable to the largest phantom.) When no grid was used, the scatter radiation caused the measurements to be in error, reducing the measured mineral content of the aluminum bar by approximately one-half or more as shown in the plate in FIG. 10. (The scatter radiation caused a greater number of photon hits at the camera than should be present, thereby causing the calculation to indicate less material between the source and the camera for stopping the photons.) However, when the cross-focussed grids were used, the measurements of mineral content showed no significant change with phantom thickness and were within 2–4% of each other. This indicates that the cross-focussed grids are very effective for scatter rejection. With the scatter problem eliminated, the gamma camera can now be used for making very accurate measurements of bone mineral even in areas of the body surrounded by a large mass of tissue, such as the abdomen.

It will be obvious to those skilled in the art that modifications may be made to the embodiment described above without departing from the scope of the present invention.

What is claimed is:

1. An attachment for a scintillation camera to enable the camera to be used for the in vivo measurement of bone mineral mass, in a living animal comprising:
    a grid holder for attachment to the camera;
    a grid mounted on said grid holder so that the grid lies directly in front of the camera when said grid holder is attached to the camera; and
    a generally U shaped arm attached at one end to said grid holder and, at the other end, including a source holder for holding a radioactive source, said source holder being entirely closed except that it defines an aperture directed toward said grid, said ends of said arm being spaced apart sufficiently to accommodate at least the portion of the body of a living animal in which the bone mineral mass is to be measured;
    wherein said source holder is at least 50 cm from said grid and said grid is focused on said source holder.

2. An attachment as recited in claim 1, wherein said aperture in said source holder is directed toward the center of said grid.

3. An attachment as recited in claim 2, wherein said grid is cross-focussed on said source holder.

4. An attachment as recited in claim 3, wherein said grid holder includes a frame which surrounds an opening, and wherein said frame defines a plurality of holes for bolting said frame to the camera, and wherein said grid is positioned so as to completely cover said opening.

5. An apparatus for the in vivo measuring of bone mineral mass in a living animal using photon absorptiometry, comprising:
    a radiation source holder;
    a scintillation camera; and
    means for reducing scatter radiation, said means comprising a grid positioned adjacent said camera between said source and said camera, said grid being focused on said source holder; said grid and source being spaced apart to accommodate at least a portion of the body of the living animal in which the bone mineral mass is to be measured.

6. An apparatus for measuring bone mineral mass as recited in claim 5, wherein the distance between said scintillation camera and said source holder is at least 50 cm.

7. An apparatus for measuring bone mineral mass as recited in claim 6, wherein said grid includes a pair of radiographic grids which are cross-focussed on said source holder.

8. An apparatus for measuring bone mineral mass as recited in claim 5, and further comprising:
    an analyzer means for storing data from said scintillation camera and calculating the bone mineral mass and areal density of a bone segment located between said source and said grid.

9. A method for the in vivo measuring of bone mineral mass, comprising:
    emitting radiation from a radiation source;
    locating a scintillation camera spaced from said source for receiving radiation from said source as it is transmitted through a plurality of points along a broad area of a bone;
    placing a grid between said source and said camera, said grid being focused on said source;
    placing a live subject between said source and said grid so that some of the radiation from said source passes through at least a portion of a bone of said subject before it passes through the grid and to the camera, with the source, subject and camera spaced apart so that the image of the bone is magnified at least two times on the camera;
    storing and analyzing the data from said camera to calculate the mass of mineral in at least a portion of the bone.

10. A method for measuring bone mineral mass as recited in claim 9, wherein the radiation which is emitted from said source is at two energy levels.

11. A method for measuring bone mineral mass as recited in claim 10, wherein said image is magnified between two and five times.

12. A method for measuring bone mineral mass in the load-bearing portion of a vertebral body, comprising:
    emitting radiation from a radiation source;
    locating a scintillation camera a distance from said source;
    reducing scatter radiation from said source by positioning a grid adjacent said camera between said source and said camera, said grid being focused on said source holder; said grid and source being spaced apart to accommodate a vertebral body in which the bone mineral mass is to be measured;
    placing a vertebral body between said source and said grid so that radiation which passes laterally from one side of said vertebral body to the other side provides a profile of said vertebral body on said scintillation camera;
    using the information provided by said scintillation camera to make a matrix of data corresponding to bone mineral mass at points along said vertebral body;
    analyzing the data in the load-bearing portions of said vertebral body to determine bone mass and areal density in the load-bearing portion of said vertebral body.

* * * * *